United States Patent [19]

Asselin et al.

[11] Patent Number: 4,522,946
[45] Date of Patent: Jun. 11, 1985

[54] DIOXY HEXAHYDROBENZO[6,7]CYCLOHEPTA[1,2,3-DE]ISOQUINOLINE DERIVATIVES USEFUL AS NEUROLEPTIC AGENTS

[75] Inventors: André A. Asselin, St. Laurent; Leslie G. Humber, Dollard des Ormeaux, both of Canada

[73] Assignee: Ayerst, McKenna & Harrison, Inc., Montreal, Canada

[21] Appl. No.: 504,014

[22] Filed: Jun. 13, 1983

[51] Int. Cl.$^3$ .................. A61K 31/435; C07D 221/18
[52] U.S. Cl. ........................ 514/284; 546/75
[58] Field of Search .................. 546/75; 424/256; 514/284

[56] References Cited

U.S. PATENT DOCUMENTS 3,403,157  9/1968  Humber et al. ............... 546/75

FOREIGN PATENT DOCUMENTS 1000701  11/1976  Canada .
1544767   5/1979  United Kingdom .

OTHER PUBLICATIONS

L. G. Humber et al., J. Heterocycl. Chem., 3, 247, (1966).
L. G. Humber et al., Can. J. Chem., 46, 2981, (1968).

*Primary Examiner*—Donald G. Daus
*Assistant Examiner*—Cecilia Shen

[57] ABSTRACT

1,2,3,7,8,12b-Hexahydrobenzo[6,7]cyclohepta[1,2,3-de]isoquinoline derivatives, characterized by having two adjacent oxy substituents at positions 4 and 5 or at positions 5 and 6, are disclosed. Thus, the substituent at position 5 is lower alkoxy or hydroxy and the substituents at positions 4 and 6 are different and are hydrogen or hydroxy. The derivatives are neuroleptic agents, free of extrapyramidal side effects. Methods for the preparation and for the use of the derivatives also are disclosed.

20 Claims, No Drawings

DIOXY HEXAHYDROBENZO[6,7]CYCLOHEPTA[1,2,3-DE]ISOQUINOLINE DERIVATIVES USEFUL AS NEUROLEPTIC AGENTS

BACKGROUND OF THE INVENTION

This invention relates to dioxy hexahydrobenzocycloheptaisoquinoline derivatives, to processes for preparing the derivatives, to pharmaceutical compositions thereof, and to methods for using the derivatives.

The dioxy derivatives have a 1,2,3,7,8,12b-hexahydrobenzo[6,7]cyclohepta[1,2,3-de]isoquinoline ring system and are characterized by having two adjacent oxy substituents on the aromatic carbocyclic portion of the isoquinoline moiety, namely at positions 4 and 5 or at positions 5 and 6.

Compounds having a 1,2,3,7,8,12b-hexahydrobenzo[6,7]cyclohepta[1,2,3-de]isoquinoline ring system have been reported: L. G. Humber and M. A. Davis, U.S. Pat. No. 3,403,157, Sept. 24, 1968 disclose such compounds wherein the ring system is optionally substituted with a variety of substituents at various positions; the compounds have antibacterial properties, the only reported activity. L. G. Humber et al., Canadian Pat. No. 1,000,701, Nov. 30, 1976 again disclose such compounds with a variety of optional substituents at various positions; the compounds are reported to be antibacterial agents and central nervous system depressants. None of the compounds claimed herein are exemplified in this patent which contains 192 pages and numerous specifically exemplified compounds. R. G. Simmonds, British Patent Specification No. 1,545,767, published May 16, 1979 discloses variously substituted 3-amino-1,2,3,7,8,12b-hexahydrobenzo[6,7]cyclohepta[1,2,3-de]isoquinoline derivatives having antiinflammatory and/or central nervous system activities. L. G. Humber et al., J. Heterocycl. Chem., 3, 247 (1966) report the preparation of 1,2,3,7,8,12b-hexahydrobenzo[6,7]cyclohepta[1,2,3-de]isoquinoline and its corresponding 4,5,10,11-tetramethoxy derivative. Also L. G. Humber et al., Can. J. Chem., 46, 2981 (1968) report a variety of N-substituted 1,2,3,7,8,12b-hexahydrobenzo[6,7]cyclohepta[1,2,3-de]isoquinolines, some of which have central nervous system activity.

In the preceding patents and publications, the 1,2,3,7,8,12b-hexahydrobenzo[6,7]cyclohepta[1,2,3-de]isoquinoline ring system is sometimes named according to a different chemical nomenclature. The chemical nomenclature used herein is the one which is currently more acceptable.

The dioxy derivatives of the present invention, characterized by their two adjacent oxy substituents, possess a valuable antipsychotic activity. Namely, the derivatives exert a neuroleptic action which is free of the extrapyramidal syndrome, a side effect usually associated with most neuroleptics. This surprising and unusual pharmacologic profile, combined with a lower order of toxicity, renders the derivatives as desirable agents for the treatment of schizophrenia.

SUMMARY OF THE INVENTION

The dioxy hexahydrobenzocycloheptaisoquinoline derivatives of this invention are represented by formula I

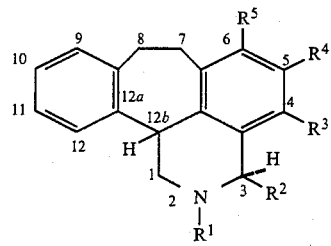

in which $R^1$ is hydrogen, lower alkyl, lower alkenyl, hydroxy(lower)alkyl or phenylmethyl; $R^2$ is hydrogen, lower alkyl, lower cycloalkyl, phenyl or phenylmethyl; $R^4$ is lower alkoxy or hydroxy; and $R^3$ is hydroxy and $R^5$ is hydrogen, or $R^3$ is hydrogen and $R^5$ is hydroxy; or a therapeutically acceptable acid addition salt thereof.

A preferred group of the dioxy derivatives of this invention is represented by formula I in which $R^1$ is lower alkyl containing one or two carbon atoms; $R^2$ is hydrogen, lower alkyl containing one to three carbon atoms, phenyl or phenylmethyl; $R^4$ is hydroxy or lower alkoxy; and $R^3$ is hydroxy and $R^5$ is hydrogen, or $R^3$ is hydrogen and $R^5$ is hydroxy; or a therapeutically acceptable acid addition salt thereof.

A more preferred group of the dioxy derivatives is represented by formula I in which $R^1$ is methyl; $R^2$ is methyl, ethyl, 1-methylethyl or phenylmethyl; $R^4$ is methoxy or hydroxy; and $R^3$ is hydroxy and $R^5$ is hydrogen, or $R^3$ is hydrogen and $R^5$ is hydroxy; or a therapeutically acceptable acid addition salt thereof.

A most preferred group is represented by formula I in which $R^1$ is methyl, $R^2$ is ethyl or phenylmethyl, $R^3$ is hydroxy, $R^4$ is methoxy and $R^5$ is hydrogen; or a therapeutically acceptable acid addition salt thereof.

Another aspect of this invention involves a method of producing neuroleptic effects without eliciting extrapyramidal syndrome, which comprises administering to said mammal an effective neuroleptic amount of a compound of formula I, or a therapeutically acceptable acid addition salt thereof.

Still another aspect of this invention involves a pharmaceutical composition comprising a compound of formula I, or a therapeutically acceptable acid addition salt thereof, and a pharmaceutically acceptable carrier.

DETAILS OF THE INVENTION

The dioxy hexahydrobenzocycloheptaisoquinoline derivatives of this invention are capable of forming acid addition salts with therapeutically acceptable acids. An acid addition salt can be prepared by reacting the base form of a derivative with either one equivalent or preferably an excess of an appropriate acid in an organic solvent, e.g. diethyl ether or an ethanol-diethyl ether mixture. Such salts may advantageously be used for the purpose of isolating and/or purifying the compounds of this invention and, if not therapeutically acceptable acid addition salts, may be transformed in a manner known into the corresponding salts with therapeutically acceptable acids. The therapeutically acceptable acid addition salts, when administered to mammals, exhibit the same pharmacologic activities as the corresponding bases. For many purposes it is preferable to administer the salts rather than the base compounds. Among the acid addition salts suitable for administration are salts such as the sulfate, phosphate, lactate, tartrate, maleate, citrate and hydrochloride. Both the base compounds and the therapeutically acceptable acid addition salts have the distinct advantage of possessing a relatively low order of toxicity.

The term "lower alkyl" as used herein means straight chain alkyl radicals containing from one to six carbon atoms and branched chain alkyl radical containing up to four carbon atoms and includes methyl, ethyl, propyl, 1-methylethyl, butyl, 2-methylpropyl and 1,1-dimethylethyl. Preferred lower alkyl radicals contain one to three carbon atoms unless stated otherwise.

The term "lower alkoxy" as used herein means a straight chain alkoxy radical containing from one to six carbon atoms, preferably one to three carbon atoms, or a branched chain alkoxy radical containing three or four carbon atoms, and includes methoxy, ethoxy, 1-methylethoxy, butoxy and hexanoxy.

The term "complex borohydride" as used herein means the metal borohydrides, including sodium borohydride, sodium cyanoborohydride, potassium borohydride, lithium borohydride, lithium triethylborohydride, zinc borohydride and the like, and metal trihydrocarbylborohydrides including lithium 9-alkyl-9-borobicyclo[3,3]nonylhydride, in which the alkyl contains one to seven carbon atoms, preferably lithium 9-tert-butyl-9-borobicyclo[3,3]nonylhydride.

The term "halo" or "halide" as used herein means a halo radical selected from bromo, chloro and iodo.

The term "hydrohalic acid" as used herein means a commercially available, concentrated solution of hydrogen chloride, hydrogen bromide or hydrogen chloride in water.

The term "lower alkanol" as used herein means both straight and branched chain alkanols containing from one to four carbon atoms and includes methanol, ethanol, 1-methylethanol and butanol.

The dioxy derivatives of this invention effect a neuroleptic action without the extrapyramidal side effects usually associated with most neuroleptics. To date, only a few neuroleptics have shown this unusual pharmacological profile; for example, clozapine, A. C. Sayers and H. A. Amsler in "Pharmacological and Biochemical Properties of Drug Substances", Vol. 1, M. E. Goldberg, Ed., American Pharmaceutical Association and Academy of Pharmaceutical Sciences, Washington, D.C., U.S.A., 1977, p 1. This particular profile for the dioxy derivatives can be demonstrated in pharmacological tests for evaluating psychomotor inhibition and cataleptic effects.

More particularly, the ability of the dioxy derivatives to effect a neuroleptic action was demonstrated in the conditioned avoidance response test (CAR), a test described by C. Morpurgo, Psychopharmacologia (Berl.), 8, 91 (1965). The results from this test for several exemplified dioxy derivatives are listed in Table I. The results are expressed therein as the intraperitoneal dose, in milligrams per kilogram of body weight of the animal, which caused a 50% failure in avoidance response (CAR, $ED_{50}$).

The lack of cataleptic activity of the dioxy derivative was demonstrated by their ability to antagonize tremorine-induced tremors in mice according to the test of P. S. J. Spencer, Brit. J. Pharmacol., 25, 442 (1965). The results for the exemplified dioxy derivatives are shown in Table I as the intraperitoneal dose, expressed in milligrams per kilogram of body weight of the animal, which caused a 50% inhibition of tremorine induced tremors (ITIT, $ED_{50}$).

TABLE I

| Compound of Formula I | | | | | Example In Experimental Describing Preparation | CAR, $ED_{50}$ (mg/kg, i.p.) | ITIT, $ED_{50}$ (mg/kg, i.p.) |
|---|---|---|---|---|---|---|---|
| $R^1$ | $R^2$ | $R^3$ | $R^4$ | $R^5$ | | | |
| $CH_3$ | $CH_3$ | OH | OH | H | 22 | 4.4 ± 2.0 | 13 ± 10.4 |
| $CH_3$ | $C_2H_5$ | OH | OH | H | 23 | 1.5 ± 0.4 | 18 ± 7.6 |
| $CH_3$ | n-$C_3H_7$ | OH | OH | H | 24 | 4.4 ± 1.4 | 11 ± 4.3 |
| $CH_3$ | i-$C_3H_7$ | OH | OH | H | 25 | 2.4 ± 0.6 | 17.5 ± 6.0 |
| $CH_3$ | $CH_2C_6H_5$ | OH | OH | H | 26 | 1.6 ± 0.3 | 22 ± 5.7 |
| $CH_3$ | $C_2H_5$ | H | OH | OH | 32 | 4.2 ± 0.4 | 21 ± 1.6 |
| $CH_3$ | $CH_2C_6H_5$ | H | OH | OH | 33 | 2.0 ± 0.2 | 9.2 ± 7.2 |
| $CH_3$ | $CH_2C_6H_5$ | OH | $OCH_3$ | H | 37 | 5.4 ± 1.8 | 8.2 ± 2.4 |
| $CH_3$ | $C_2H_5$ | OH | $OCH_3$ | H | 44 | 3.0 ± 0.8 | 6.8 ± 2.0 |

The above results demonstrate that the present dioxy derivatives effect a potent motor inhibiting action, characteristic of neuroleptics; but unlike most neuroleptics, the dioxy derivatives lack cataleptic activity as shown by their ability to antagonize induced tremors. This surprising and unexpected pharmacological profile of the present dioxy derivatives becomes even more evident in view of the contrasting finding that corresponding 10,11-dihydroxy analogous derivatives exhibit relatively weak activity in the CAR test and are completely ineffective in antagonizing tremorine induced tremors.

When the dioxy derivatives of this invention are used as neuroleptic agents in mammals, e.g. rats and mice, they are used alone or in combination with pharmacologically acceptable carriers, the proportion of which is determined by the solubility and chemical nature of the compound, chosen route of administration and standard biological practice. For example, they may be administered orally, or parenterally by injection.

For administration to a mammal by parenteral injection, it is preferred to use the compounds of formula I in solution in a sterile aqueous vehicle which may also contain other solutes such as buffers or preservatives, as well as sufficient quantities of pharmaceutically acceptable salts or of glucose to make the solution isotonic.

When the compounds of this invention are employed orally as neuroleptic agents in mammals, orally effective, neuroleptic amounts of the compounds are administered to the mammal, either alone or combined with pharmaceutically acceptable excipients in a dosage form, i.e. capsule or tablet, or the compounds are administered orally in the form of a solution or a suspension.

The tablet compositions contain the active ingredient in admixture with non-toxic pharmaceutical excipients known to be suitable in the manufacture of tablets. Suitable pharmaceutical excipients are, for example, starch, milk, sugar, certain types of clay and so forth. The tablets may be uncoated or they may be coated by known techniques so as to delay disintegration and absorption in the gastrointestinal tract and thereby provide a sustained action over a longer period.

The aqueous suspensions of the invention contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions may also contain one or more preservatives, one or more coloring agents, one or more flavoring agents and one or more sweetening agents.

Non-aqueous suspension may be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions may also contain a sweetening agent, a flavoring agent and an antioxidant.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered for neuroleptic purposes at a concentration level that will generally afford effective results without causing any harmful or deleterious side effects, for example, catalepsy, and preferably at a level that is in a range of from about 0.1 mg to about 50 mg per kilogram of body weight per day, although as aforementioned variations will occur. However, a dosage level that is in the range of from about 0.1 mg to about 20 mg per kilogram of body weight per day is most desirably employed in order to achieve effective results.

PROCESS

A starting material for preparing the dioxy derivatives of this invention is the Schiff base of formula II

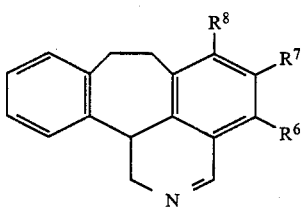

in which $R^6$ and $R^7$ are both lower alkoxy and $R^8$ is hydrogen, or $R^6$ is hydrogen and $R^7$ and $R^8$ are both lower alkoxy. Using appropriately substituted di(lower-)alkoxydibenzo[a,d]cyclohepten-5-one derivatives, the process described for 1,7,8,12b-tetrahydrobenzo[6,7]cyclohepta[1,2,3-de]isoquinoline (i.e. the compound which is represented by formula II in which $R^6$, $R^7$ and $R^8$ are each hydrogen), described by F. T. Bruderlein and L. G. Humber, U.S. Pat. No. 3,985,751, issued Oct. 12, 1976, can be used to prepare the Schiff bases of formula II having two adjacent lower alkoxy groups at positions 4 and 5, or at positions 5 and 6.

The Schiff base is transformed into the key intermediate of formula

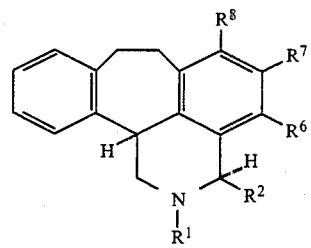

in which $R^1$ and $R^2$ are as defined herein, and $R^6$ and $R^7$ are both lower alkoxy and $R^8$ is hydrogen, or $R^6$ is hydrogen and $R^7$ and $R^8$ are both lower alkoxy, by one of the following processes listed hereinafter in sections (a) to (d):

(a) reducing the Schiff base of formula II with a complex borohydride to obtain the corresponding compound of formula III in which $R^1$ and $R^2$ are both hydrogen, and $R^6$ and $R^7$ are both lower alkoxy and $R^8$ is hydrogen, or $R^6$ is hydrogen and $R^7$ and $R^8$ are both lower alkoxy; or (b) reacting the Schiff base of formula II with an organic halide of formula $R^1$—X in which $R^1$ is lower alkyl, lower alkenyl, hydroxy(lower)alkyl or phenylmethyl and X is halo to obtain the quaternary salt of formula IV

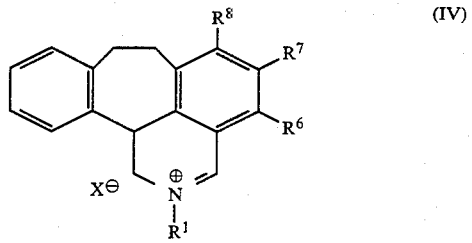

in which $R^1$ is lower alkyl, lower alkenyl, hydroxy(lower)alkyl or phenylmethyl; $R^6$ and $R^7$ are both lower alkoxy and $R^8$ is hydrogen, or $R^6$ is hydrogen and $R^7$ and $R^8$ are both lower alkoxy; and X is halo; and reducing the quaternary salt with a complex borohydride to obtain the corresponding compound of formula III in which $R^1$ is lower alkyl, lower alkenyl, hydroxy(lower-)alkyl or phenylmethyl; $R^2$ is hydrogen; and $R^6$ and $R^7$ are both lower alkoxy and $R^8$ is hydrogen, or $R^6$ is hydrogen and $R^7$ and $R^8$ are both lower alkoxy; or (c) reacting the quaternary salt of formula IV in which $R^1$ is lower alkyl, lower alkenyl, hydroxy(lower-)alkyl or phenylmethyl; and $R^6$ and $R^7$ are both lower alkoxy and $R^8$ is hydrogen, or $R^6$ is hydrogen and $R^7$ and $R^8$ are both lower alkoxy; with a reagent of formula $R^2$—Y in which $R^2$ is lower alkyl, lower cycloalkyl, phenyl or phenylmethyl and Y is Mg-(halo) or Li to obtain the corresponding compound of formula III in which $R^1$ is lower alkyl, lower alkenyl, hydroxy(lower-)alkyl or phenylmethyl; $R^2$ is lower alkyl, lower cycloalkyl, phenyl or phenylmethyl; and $R^6$ and $R^7$ are both lower alkoxy and $R^8$ is hydrogen, or $R^6$ is hydrogen and $R^7$ and $R^8$ are both lower alkoxy; or (d) reducing a compound of formula III in which $R^1$ is phenylmethyl, $R^2$ is lower alkyl, lower cycloalkyl, phenyl or phenylmethyl, and $R^6$, $R^7$ and $R^8$ are as defined in the last instance with hydrogen in the presence of a noble metal hydrogenation catalyst to obtain the corresponding compound of formula III in which $R^1$ is hydrogen, $R^2$ is lower alkyl, lower cycloalkyl, phenyl or phenylmethyl, and $R^6$ and $R^7$ are both lower alkoxy and $R^8$ is hydrogen, or $R^6$ is hydrogen and $R^7$ and $R^8$ are both lower alkoxy.

More particularly, with reference to the preceding section (a), the key intermediates of formula III in which $R^1$ and $R^2$ are both hydrogen, and $R^6$ and $R^7$ are both lower alkoxy and $R^8$ is hydrogen or $R^6$ is hydrogen and $R^7$ and $R^8$ are both lower alkoxy are prepared by reducing the Schiff base of formula II with a molar excess of a complex borohydride, for example sodium borohydride or cyanoborohydride, in an inert solvent. Suitable inert solvents include tetrahydrofuran, or lower alkanols, preferably methanol, ethanol or 2-propanol. An inert solvent consisting of a mixture of methanol or ethanol with a small amount of added chloroform (0.5 to 5%, v/v), to increase the solubility characteristics of the solvent, has been found to be practical and advantageous for performing the reduction. The reduction usually is performed at temperatures ranging from 0° C. to the boiling point of the reaction mixture for 30 minutes to three hours. When sodium cyanoborohydride is used, the reduction is preferably performed at or near a pH of 4, for example in the presence of acetic acid. The preferred complex borohydride is sodium borohydride.

With reference to section (b), the key intermediates of formula III in which $R^1$ is lower alkyl, lower alkenyl, hydroxy(lower)alkyl or phenylmethyl; $R^2$ is hydrogen; and $R^6$ and $R^7$ are both lower alkoxy and $R^8$ is hydrogen, or $R^6$ is hydrogen and $R^7$ and $R^8$ are both lower alkoxy; are prepared by reacting the Schiff base of formula II with at least one equivalent, preferably an excess, of an organic halide of formula $R^1$—X in which $R^1$ is as defined in the last instance and X is halo in an inert organic solvent. Suitable organic solvents are acetone, methanol, ethanol, benzene or diethyl ether. The reaction usually is performed at an elevated temperature ranging from 40° to 100° C., or at the boiling point of the organic solvent, and for a period of ten minutes to six hours. In this manner, the corresponding quaternary salt of formula IV is obtained. Thereafter, the quaternary salt is reduced with a complex borohydride in the same manner and described above for the Schiff base to give the desired intermediate of formula III.

With reference to section (c), the intermediates of formula III in which $R^1$ is lower alkyl, lower alkenyl, hydroxy(lower)alkyl or phenylmethyl; $R^2$ is lower alkyl, lower cycloalkyl, phenyl or phenylmethyl; and $R^6$ and $R^7$ are both lower alkoxy and $R^8$ is hydrogen, or $R^6$ is hydrogen and $R^7$ and $R^8$ are both lower alkoxy; can be obtained by reacting the quaternary salt of formula IV with an appropriate Grignard reagent of the formula $R^2$—Y in which $R^2$ is lower alkyl, lower cycloalkyl, phenyl or phenylmethyl and Y is Mg-(halo) in an inert solvent, for example, diethyl ether or tetrahydrofuran, according to the conditions of the Grignard reaction. In this manner, the desired, corresponding intermediate of formula III is obtained. Suitable reaction times and temperatures range from 15 minutes to 24 hours and from −40° to 90° C.; respectively.

Alternatively, the quaternary salt of formula IV is reacted with an appropriate organolithium reagent of $R^2$—Y in which $R^2$ is lower alkyl, lower cycloalkyl, phenyl or phenylmethyl and Y is Li under the same conditions as described for the Grignard reaction to give the intermediate of formula III.

The above reaction of the quaternary salt of formula IV with a Grignard reagent or organolithium affords mainly the corresponding intermediate of formula III wherein the substituent ($R^2$) at position 3 is cis to the hydrogen at position 12b. Hence, transformation of this particular intermediate of formula III into the corresponding compound of formula I in which $R^2$ is lower alkyl, lower cycloalkyl, phenyl or phenylmethyl affords the compounds with a 3,12b-cis configuration with respect to the substituent at position 3 and the hydrogen at position 12b, or, in other words, a 3,12b-trans configuration with respect to the hydrogens at position 3 and 12b. Compounds of formula I and III having this stereochemical relationship are designated herein as "(3,12b-trans)".

With reference to section (d), the intermediates of formula III in which $R^1$ is hydrogen; $R^2$ is lower alkyl, lower cycloalkyl, phenyl or phenylmethyl; and $R^6$ and $R^7$ both are lower alkoxy and $R^8$ is hydrogen, or $R^6$ is hydrogen and $R^7$ and $R^8$ both are lower alkoxy; are obtained by reducing the corresponding compound of formula III in which $R^1$ is phenylmethyl in the presence of a noble catalyst, for example, platinum on carbon, palladium on charcoal or platinum oxide, in an inert solvent, for example, methanol, ethanol or acetic acid.

Turning now to the transformation of the key intermediate of formula III to the final products, the dioxy derivatives of formula I, the dioxy derivatives are obtained by:

(A) dealkylating the intermediate of formula III in which $R^1$ is hydrogen, lower alkyl, lower alkenyl, hydroxy(lower)alkyl or phenylmethyl; $R^2$ is hydrogen, lower alkyl, lower cycloalkyl, phenyl or phenylmethyl; and $R^6$ and $R^7$ are both lower alkoxy and $R^8$ is hydrogen, or $R^6$ is hydrogen and $R^7$ and $R^8$ are both lower alkoxy; with a hydrohalic acid or with boron tribromide to obtain the corresponding compound of formula I in which $R^1$ is hydrogen, lower alkyl, lower alkenyl, hydroxy(lower)alkyl or phenylmethyl; $R^2$ is hydrogen, lower alkyl, lower cycloalkyl, phenyl or phenylmethyl, and $R^3$ and $R^4$ are both hydroxy and $R^5$ is hydrogen, or $R^3$ is hydrogen and $R^4$ and $R^5$ are both hydroxy; or (B) selectively dealkylating the intermediate of formula III in which $R^1$ is hydrogen, lower alkyl, lower alkenyl, hydroxy(lower)alkyl or phenylmethyl; $R^2$ is hydrogen, lower alkyl, lower cycloalkyl, phenyl or phenylmethyl; and $R^6$ and $R^7$ are both lower alkoxy and $R^8$ is hydrogen, or $R^6$ is hydrogen and $R^7$ and $R^8$ are both lower alkoxy; with concentrated hydriodic acid at 0° to 30° C., with concentrated hydrochloric acid at 90° to 109° C., or with methanesulfonic acid in the presence of methionine to obtain the corresponding compound of formula I in which $R^1$ is hydrogen, lower alkyl, lower alkenyl, hydroxy(lower)alkyl or phenylmethyl; $R^2$ is hydrogen, lower alkyl, lower cycloalkyl, phenyl or phenylmethyl; and $R^3$ is hydroxy, $R^4$ is lower alkoxy and $R^5$ is hydrogen, or $R^3$ is hydrogen, $R^4$ is lower alkoxy and $R^5$ is hydroxy; and (C) if desired, forming the corresponding therapeutically acceptable acid addition salt of the compound of formula I.

More particularly, with reference to preceding section A, the compounds of formula I in which $R^1$ and $R^2$ are as defined herein, and $R^3$ and $R^4$ are both hydroxy and $R^5$ is hydrogen, or $R^3$ is hydrogen and $R^4$ and $R^5$ are both hydroxy, are obtained by dealkylating the corresponding dialkoxy intermediate of formula III. The dealkylation can be performed in a concentrated hydrohalic acid, preferably concentrated hydrochloric acid (33 to 38% by weight/volume of hydrogen chloride in water), concentrated hydrobromic acid (40 to 50% by weight/volume of hydrogen bromide in water) or preferably by concentrated hydriodic acid (47 to 57% by weight/volume of hydrogen iodide in water). The time and temperature ranges for this reaction are variable and depend on the nature of the starting material and the hydrohalic acid employed. The reaction is usually performed at 80° C. to the boiling point of the reaction mixture and the course of the reaction is monitored by subjecting aliquots of the reaction mixture to thin layer chromatography to determine the required reaction time for completion of the reaction.

Under such circumstances, for example, a reaction time of one to three hours generally is required to effect dealkylation when 47-57% (w/v) hydriodic acid is employed at reaction temperatures ranging from 110° to 127° C.

Preferably, the dealkylation is done by reacting the corresponding dialkoxy compound of formula III with an effective amount of boron tribromide, usually two to ten molar equivalents, at −20° to 20° C. for 30 minutes to three hours in an inert solvent, for example, chloroform or methylene dichloride. Thereafter, the reaction mixture is cooled to about −40° C. to 0° C. and excess boron tribromide is decomposed and the orthoboric ester of the product is hydrolyzed with a lower alkanol, preferably methanol or ethanol. The desired compound of formula I can be isolated thereafter by precipitating the compound from solution with a non-polar solvent, for instance diethyl ether or hexane.

With reference to preceding section B, the compounds of formula I in which $R^1$ and $R^2$ are as defined herein, and $R^3$ is hydroxy, $R^4$ is lower alkoxy and $R^5$ is hydrogen, or $R^3$ is hydrogen, $R^4$ is lower alkoxy and $R^5$ is hydroxy, are obtained by selectively dealkylating the corresponding dialkoxy intermediate of formula III. This selective dealkylation generally can be performed by reacting the dialkoxy compound of formula III with concentrated hydriodic acid at 0° to 30° C. for one to three weeks, or with concentrated hydrochloric acid at 90° to 109° C. for about 10 to 24 hours. In such instances, the course of the reaction is followed by thin layer chromatography techniques and is stopped when only a trace of starting material remains in the reaction mixture and a small amount of the corresponding completely dealkylated derivative begins to form. The preferential dealkylation, however, can be performed best by subjecting the dialkoxy compound of formula I to the action of the methanesulfonic acid in the presence of methionine according to the method described by F. Nobutaka, I. Hiroshi and Y. Haruaki, J. Chem. Soc., Perkin 1, 2288 (1977). This latter reaction is best performed at 20° to 25° C. for one to three days using an excess of methanesulfonic acid as the solvent.

The following examples illustrate further this reaction.

EXAMPLE 1

N-Formyl-(2,3-dimethoxy-10,11-dihydro-5H-dibenzo[a,d]cyclohepten-5-yl)methylamine A 250 mL three-necked flask was charged under nitrogen with magnesium (9.6 g, 0.4 mol), mercuric chloride (0.4 g) and dry tetrahydrofuran (70 mL). The mixture was cooled to −10° C. to −20° C. and a solution of freshly distilled chloromethylethyl ether (37.6 ml, 0.4 mol) in dry tetrahydrofuran (70 mL) was added dropwise within 0.5 hr. at −15° C. The mixture was stirred at that temperature for 5 hr., and then cooled to −40° C. The cooled solution was removed by a syringe and added to a stirred suspension of 2,3-dimethoxy-10,11-dihydro-5H-dibenzo[a,b]cyclohepten-5-one (53.6 g, 0.2 mol), described by S. O. Winthrop et al., J. Org. Chem., 27, 230 (1962), in tetrahydrofuran (300 mL) at −10° C. The reaction mixture was stirred at that temperature for one hour during which the suspension turned into a clear greenish solution. The solution was allowed to warm up to 20°-22° C. over 18 hr. and then poured onto ice and water containing ammonium chloride (22 g). The solution was saturated with sodium chloride and extracted with diethyl ether. The organic layer was washed with sodium chloride solution, dried, and evaporated to give a yellow oil. Crystallization of the oil from pentane gave 5-(ethoxymethyl)-2,3-dimethoxy-10,11-dihydro-5H-dibenzo[a,d]cyclohepten-5-ol as a pale yellow solid (59 g) of sufficient purity for the next step. A pure sample of the latter compound, prepared by two additional crystallizations of the pale yellow solid from chloroform-hexane, had mp 98°-100° C. and IR ($CHCl_3$) 3520, 2840, 1255, 1110 $cm^{-1}$.

The latter compound (58 g, 0.18 mol) was dissolved in formic acid (110 mL, 98%). The solution was kept at 20°-22° C. for 2.5 hr. and then heated at steam bath temperature for 3 hr. The solution was then poured into ice water. The resulting precipitate was collected, washed with water and dried to give 2,3-dimethoxy-10,11-dihydro-5H-dibenzo[a,d]cycloheptene-5-carboxaldehyde, as an off-white solid (36 g) of sufficient purity for the next step. A pure sample of the latter compound prepared by crystallization from chloroform and hexane, had mp 130°-132° C. and IR ($CHCl_3$) 2830, 1718, 1255, 1112 $cm^{-1}$.

The latter compound (35 g, 0.125 mol) was suspended in a mixture of hydroxylamine hydrochloride (15.8 g, 0.22 mol) in ethanol (170 mL) and water (50 mL). The suspension was cooled in an ice bath. Powdered sodium hydroxide (31.6 g, 0.8 mol) was added to the suspension. Thereafter, the supension was stirred vigorously at 20°-22° C. for 3 hr. Water (500 mL) was added and the mixture was stirred for an additional 18 hr. The mixture was concentrated to one-half its volume. The resulting precipitate was collected, dissolved in water and the solution rendered acidic by the dropwise addition of acetic acid (60 ml). The precipitate was collected to give 2,3-dimethoxy-10,11-dihydro-5H-dibenzo[a,d]cyclohepten-5-aldoxime as a pale yellow solid (33.4 g) of sufficient purity for the next step. A pure sample of the latter compound, prepared by two additional recrystallizations from chloroform-hexane (with charcoal treatment), had mp 176°-177° C. and IR ($CHCl_3$) 3570, 3310, 2830, 1265, 1118 $cm^{-1}$.

Raney nickel alloy (42 g) was added in one portion to a well-stirred mixture of the latter oxime (28 g, 0.094 mol) in ethanol (560 mL) and 2N aqueous sodium hydroxide (560 mL). The mixture was filtered after 2 hr. The filtrate was evaporated under reduced pressure and the residue was diluted with water. The aqueous mixture was extracted with diethyl ether. The organic extract was washed with water, dried ($MgSO_4$) and filtered. A saturated solution of hydrogen chloride in diethyl ether was added dropwise to the filtrate. The precipitate was collected, washed with diethyl ether and dried to give (2,3-dimethoxy-10,11-dihydro-5H-dibenzo[a,d]cyclohepten-5-yl)methylamine hydrochloride (27.5 g). A pure sample of the hydrochloride, prepared by recrystallization from methanol-diethyl ether, had mp 272°–275° C. and IR (white mineral oil) 2900, 1250, 1100 cm$^{-1}$.

The hydrochloride was converted quantitatively to its free base by mixing the hydrochloride with 5% aqueous sodium hydroxide, extracting the mixture with diethyl ether and concentrating the extract. The free base had mp 82°–85° C. and, because it formed a carbonate salt when exposed to the atmosphere, it was kept under nitrogen.

Formic anhydride was prepared by heating formic acid (98%, 1.13 mL) with acetic anhydride (2.9 mL) at 50°–60° C. for 2 hr. The reaction mixture of formic anhydride was cooled to 20°–22° C. and a solution of the above designated free base (4.42 g, 0.0155 mol) in dry tetrahydrofuran (30 mL) was added dropwise to the reaction mixture while maintaining the temperature below 40° C. Stirring was continued for 2 hr. The mixture was poured into ice-water. The precipitate was collected and washed with water to give the title compound (4.5 g). A pure sample of the title compound, obtained by two crystallizations from chloroform-hexane, had mp 118°–119° C. and IR (CHCl$_3$) 3440, 3350, 1685 cm$^{-1}$.

EXAMPLE 2

4,5-Dimethoxy-1,7,8,12b-tetrahydrobenzo[6,7]cyclohepta[1,2,3-de]isoquinoline (II; R$^6$ and R$^7$=OCH$_3$ and R$^8$=H) and
5,6-dimethoxy-1,7,8,12b-tetrahydrobenzo[6,7]cyclohepta[1,2,3-de]isoquinoline (II; R$^6$=H, and R$^7$ and R$^8$=OCH$_3$)

A mixture of N-formyl-(2,3-dimethoxy-10,11-dihydro-5H-dibenzo[a,d]cyclohepten-5-yl)methylamine (23 g), described in example 1, and polyphosphate ester (459 g), prepared by the procedure described by L. F. Fieser and M. Fieser in "Reagents for Organic Synthesis, John Wiley and Sons, Inc., New York, N.Y., U.S.A. 1967, p 892, in chloroform (225 mL) was stirred under nitrogen at 20°–22° C. for 48 hr. The reaction mixture was poured onto ice. The resulting mixture was rendered acidic with 10% aqueous hydrochloric acid, washed with ethyl acetate, rendered basic with cooled concentrated ammonium hydroxide and extracted with ethyl acetate. The latter extract was washed with water, dried (MgSO$_4$) and evaporated to dryness to give a yellow oil (18.5 g). The oil was subjected to chromatography on silica gel. Elution with acetonebenzene (1:9, v/v) first gave 5,6-dimethoxy-1,7,8,12b-tetrahydrobenzo[6,7]-cyclohepta[1,2,3-de]isoquinoline (1.2 g), mp 166°–167° C. (after recrystallization from a mixture of ethyl acetate, benzene and hexane), and NMR (CDCl$_3$)δ 3.80 and 3.83 (2s, 6H), 6.85 (s, 1H), 7.0–7.5 (m, 4H), 8.58 (s, 1H). Continued elution with the same eluant gave 4,5-dimethoxy-1,7,8,12b-tetrahydrobenzo[6,7]cyclohepta[1,2,3-de]isoquinoline (8.8 g), mp 131°–132° C. (after recrystallization from a mixture of ethyl acetate, benzene and hexane), NMR (CDCl$_3$) δ3.82 (s, 6H), 6.70 (s, 1H), 7.0–7.5 (m, 4H), 8.13 (s, 1H), and IR (CHCl$_3$) 1640 cm$^{-1}$.

EXAMPLE 3

4,5-Dimethoxy-1,2,3,7,8,12b-hexahydrobenzo[6,7]cyclohepta[1,2,3-de]isoquinoline (III; R$^1$, R$^2$ and R$^8$=H and R$^6$ and R$^7$=OCH$_3$)

Sodium borohydride (0.5 g) was added portionwise to a suspension of 4,5-dimethoxy-1,7,8,12b-tetrahydrobenzo[6,7]cyclohepta[1,2,3-de]isoquinoline (1.0 g, 3.3 mmol, described in example 2) in methanol (25 mL) at 0° C. The reaction mixture was stirred at 20°–22° C. for one hr. and then poured into water. The resulting mixture was extracted (2x) with diethyl ether. The extract was dried (MgSO$_4$), filtered through charcoal and evaporated to dryness affording the title compound, NMR (CDCl$_3$) δ2.0 (s, 1H), 3.78 & 3.80 (2s, 6H), 3.7 (m, 2H), 4.5 (m, 1H), 6.5–7.6 (m, 5H).

The corresponding hydrochloric acid addition salt of the title compound was prepared by adding a saturated solution of hydrogen chloride in diethyl ether to a solution of the title compound in diethyl ether, concentrating the resulting mixture to dryness and recrystallizing the residue from ethanol. The pure addition salt (hydrochloride) had mp>260° C.; IR (white mineral oil) 2700 cm$^{-1}$; Anal Calcd for C$_{19}$H$_{21}$NO$_2$.HCl: C, 68.77% H, 6.68% N, 4.22%; Found: C, 68.80% H, 6.74% N, 4.36%.

EXAMPLE 3a

By following the procedure of example 3, but replacing 4,5-dimethoxy-1,7,8,12b-tetrahydrobenzo[6,7]cyclohepta[1,2,3-de]isoquinoline with an equivalent amount of 5,6-dimethoxy-1,7,8,12b-tetrahydrobenzo[6,7]cyclohepta[1,2,3-de]isoquinoline, described in example 2; 5,6-dimethoxy-1,2,3,7,8,12b-hexahydrobenzo[6,7]cyclohepta[1,2,3-de]isoquinoline, NMR (CDCl$_3$)δ 1.9 (s, 1H), 3.8 (2s, 6H), 4.4 (m, 1H), 6.6 (s, 1H), 7.15 (m, 4H), was obtained. The corresponding hydrochloride of the latter compound had mp>250° C., IR (white mineral oil) 2600 cm$^{-1}$; Anal Calcd for C$_{19}$H$_{21}$NO$_2$.HCl: C, 68.77% H, 6.68% N, 4.22%; Found: C, 68.25% H, 6.75% N, 3.98%.

EXAMPLE 4

4,5-Dimethoxy-2-methyl-1,2,3,7,8,12b-hexahydrobenzo[6,7]cyclohepta[1,2,3-de]isoquinoline (III; R$^1$=CH$_3$, R$^2$ and R$^8$=H and R$^6$ and R$^7$=OCH$_3$)

(a) Preparation of Schiff base quaternary salt:

The organic halide, methyl iodide (5 mL), was added to a solution of 4,5-dimethoxy-1,7,8,12b-tetrahydrobenzo[6,7]cyclohepta[1,2,3-de]isoquinoline (3.0 g, 10 mmol; described in example 2) in acetone (75 mL). The mixture was heated at reflux (reflux time=1 hr.), cooled to 0° C. and diluted with diethyl ether. The solid (isoquinolinium salt) was collected and dried under vacuum to give 4,5-dimethoxy-2-methyl-1,7,8,12b-tetrahydrobenzo[6,7]cyclohepta[1,2,3-de]isoquinolinium iodide, mp 179°–182° C.

(b) Reduction:

A suspension of the latter isoquinolinium salt (2.4 g) in methanol (50 mL) was cooled to 0° C. Sodium borohydride (0.40 g) was added to the suspension. A white solid immediately began to crystallize out of the reaction mixture. After stirring at 20°–22° C. for 30 min., the reaction mixture was diluted with water. The solid was collected on a filter and recrystallized from methanol to give the title compound; mp 128°–129° C.; NMR (CDCl$_3$) δ2.51 (s, 3H), 3.70 (s, 3H), 3.75 (s, 3H), 4.50 (broad, 1H), 6.37 (s, 1H), 7.05 (m, 3H), 7.50 (m, 1H); Anal Calcd for C$_{20}$H$_{23}$NO$_2$: C, 77.64% H, 7.49% N, 4.53%; Found: C, 77.74% H, 7.47% N, 4.40%.

EXAMPLE 4a

By following the two step procedure of example 4, but replacing methyl iodide with an equivalent amount of ethyl iodide, 2-ethyl-4,5-dimethoxy-1,2,3,7,8,12b-hexahydrobenzo[6,7]cyclohepta[1,2,3-de]isoquinoline; mp 105°–106° C.; NMR (CDCl$_3$) δ 1.29 (t, J=7 Hz, 3H), 2.65 (t, J=7 Hz, 2H), 3.69 & 3.73 (2s, 6H), 4.55 (t, J=4 Hz, 1H), 6.41 (s, 1H), 7.10 (m, 3H), 7.35 (m, 1H); Anal Calcd for $C_{21}H_{25}NO_2$: C, 77.98% H, 7.79% N, 4.33%; Found: C, 78.17% H, 8.21% N, 4.33%, was obtained via the quaternary Schiff base, 2-ethyl-4,5-dimethoxy-1,7,8,12b-tetrahydrobenzo[6,7]cyclohepta[1,2,3-de]isoquinolinium iodide, mp 179°–181° C.; NMR (CDCl$_3$) δ 1.78 (t, 3H), 3.84 & 3.92 (2s, 6H), 5.25 (m, 1H), 6.9–7.4 (m, 4H), 7.8 (s, 1H), 10.0 (s, 1H); IR (CHCl$_3$) 1660 cm$^{-1}$.

EXAMPLE 4b

By following the two step procedure of example 4, but replacing methyl iodide with 1-iodopropane and using a reflux time of 18 hr., 4,5-dimethoxy-2-propyl-1,2,3,7,8,12b-hexahydrobenzo[6,7]cyclohepta[1,2,3-de]isoquinoline; mp 100°–102° C.; NMR (CDCl$_3$)δ 1.03 (t, J=7 Hz, 3H), 3.70 (s, 3H), 3.75 (s, 3H), 4.51 (t, 1H), 6.40 (s, 1H), 7.10 (m, 3H), 7.60 (m, 1H); Anal Calcd for $C_{22}H_{27}NO_2$: C, 78.30% H, 8.07% N, 4.15%; Found: C, 78.36% H, 8.17% N, 4.18%; was obtained.

EXAMPLE 4c

By following the two step procedure of example 4, but replacing methyl iodide with 2-iodopropane and using a reflux period of 24 hr., 4,5-dimethoxy-2-(1-methylethyl)-1,2,3,7,8,12b-hexahydrobenzo[6,7]cyclohepta[1,2,3-de]isoquinoline; NMR (CDCl$_3$) δ1.21 (2d, J=7 Hz, 6H), 3.67 (s, 3H), 3.74 (s, 3H), 4.51 (t, 1H), 6.41 (s, 1H), 7.10 (m, 3H), 7.55 (m, 1H); was obtained. The corresponding hydrochloride of the latter compound had mp 221°–224° C.; Anal Calcd for $C_{22}H_{27}NO_2.HCl$: C, 70.66% H, 7.55% N, 3.75%; Found: C, 70.34% H, 7.53 N, 3.72.

EXAMPLE 4d

By following the two step procedure of example 4, but replacing methyl iodide with allyl bromide and using a reflux period of 18 hr., 2-(2-propenyl)-4,5-dimethoxy-1,2,3,7,8,12b-hexahydrobenzo[6,7]cyclohepta[1,2,3-de]isoquinoline; mp 123°–125° C.; NMR (CDCl$_3$)δ 3.71 & 3.75 (s, 6H), 4.55 (t, J=3.8 Hz, 1H), 5.3 (m, 2), 6.0 (m, 1H), 6.4 (s, 1H), 7.05 (m, 3H), 7.6 (m, 1H); Anal Calcd for $C_{22}H_{25}NO_2$: C, 78.77% H, 7.51% H, 4.18%; Found: C, 78.73% H, 7.58% N, 4.16%; was obtained.

EXAMPLE 4e

By following the two step procedure of example 4, but replacing methyl iodide with iodoethanol, using a reflux period of 18 hr. and performing the final isolation by extraction with diethyl ether, 4,5-dimethoxy-1,2,3,7,8,12b-hexahydrobenzo[6,7]cyclohepta[1,2,3-de]isoquinoline-2-ethanol; mp 123°–124° C. (after recrystallization from diethyl-ether-hexane); NMR (CDCl$_3$) δ 3.70 (s, 3H), 3.75 (s, 3H), 4.5 (t, J=4.5 Hz, 1H), 6.35 (s, 1H), 7.2 (m, 4H); Anal Calcd for $C_{21}H_{25}NO_3$: C, 74.31% H, 7.42% N, 4.13%; Found: C, 74.23% H, 7.43% N, 4.11%; was obtained.

EXAMPLE 4f

By following the two step procedure of example 4, but replacing methyl iodide with benzyl bromide and using a reflux period of 18 hr., 4,5-dimethoxy-2-(phenylmethyl)-1,2,3,7,8,12b-hexahydrobenzo[6,7]cyclohepta[1,2,3-de]isoquinoline; mp 131°–133° C.; NMR (CDCl$_3$) δ 3.76 (s, 3H), 3.69 (s, 3H), 4.47 (m, 1H), 6.27 (s, 1H), 7.0–7.5 (m, 9H); Anal Calcd for $C_{26}H_{27}NO_2$: C, 81.01% H, 7.06% N, 3.63%; Found: C, 80.91% H, 7.17% N, 3.63%; was obtained.

EXAMPLE 5

5,6-Dimethoxy-2-methyl-1,2,3,7,8,12b-hexahydrobenzo[6,7]cyclohepta[1,2,3-de]isoquinoline (III; $R^1$=CH$_3$, $R^2$ and $R^6$=H, and $R^7$ and $R^8$=OCH$_3$)

(a) Preparation of quaternary Schiff base:

Methyl iodide (20 mL) was added to a solution of 5,6-dimethoxy-1,7,8,12b-tetrahydrobenzo[6,7]cyclohepta[1,2,3-de]isoquinoline (8.7 g, 29 mmol, described in example 2) in acetone (150 mL). The mixture was heated at reflux (reflux time=30 min.). After cooling, diethyl ether was added to the mixture. The solid material in the mixture was collected and dried to give 5,6-dimethoxy-2-methyl-1,7,8,12b-tetrahydrobenzo[6,7]cyclohepta[1,2,3-de]isoquinolinium iodide (11.8 g), a sample of which had mp 195°–210° C. after successive recrystallizations from acetone and methanol-diethyl ether.

(b) Reduction:

Sodium borohydride (2.0 g, 5 mmol) was added portionwise to the latter isoquinolinium salt (7.3 g, 17 mmol) suspended in methanol (50 mL) at 4° C. At one point during the addition a clear solution was obtained, then a precipitate began to form. After the addition, the reaction mixture was stirred for 1.5 hr. at 0° C., diluted with water and then stirred for 18 hr. at 20°–22° C. The resulting solid was collected and dried to give the title compound (4.75 g); mp 129°–130° C. (after recrystallization from methanol); NMR (CDCl$_3$) δ 2.53 (s, 3H), 3.75 (s, 6H), 4.5 (broad, 1H), 6.48 (s, 1H), 7.3 (m, 4H); Anal Calcd for $C_{20}H_{23}NO_2$: C, 77.64% H, 7.49% N, 4.53%; Found: C, 77.30% H, 7.66% N, 4.48%.

EXAMPLE 5a

By following the two step procedure of example 5, but replacing methyl iodide with an equivalent amount of ethyl iodide, 2-ethyl-5,6-dimethoxy-1,2,3,7,8,12b-hexahydrobenzo[6,7]cyclohepta[1,2,3-de]isoquinoline; mp 98°–100° C.; NMR (CDCl$_3$) δ 1.3 (t, J=7 Hz, 3H), 3.75 (s, 6H), 4.5 (t, J=3.5 Hz, 1H), 6.45 (s, 1H), 7.05 (m, 3H), 7.5 (m, 1H); Anal Calcd for $C_{21}H_{25}NO_2$: C, 77.98% H, 7.79% N, 4.33%; Found: C, 78.11% H, 7.77% N, 4.30%; was obtained.

EXAMPLE 6

(3,12b-trans)-4,5-Dimethoxy-2,3-dimethyl-1,2,3,7,8,12b-hexahydrobenzo[6,7]cyclohepta[1,2,3-de]isoquinoline (III; $R^1$ and $R^2$=CH$_3$, $R^6$ and $R^7$=OCH$_3$ and $R^8$=H)

A solution of the Grignard reagent, methyl magnesium iodide [prepared from magnesium (194 mg, 8 mmol) and methyl iodide (0.6 ml)] in diethyl ether (10 mL), was added via a syringe to a stirred suspension of 4,5-dimethoxy-2-methyl-1,7,8,12b-tetrahydrobenzo[6,7]cyclohepta[1,2,3-de]isoquinolinium iodide (1.1 g, 2.5 mmol, described in example 4) in diethyl ether (10 mL). The reaction mixture was stirred for 30 min. and then poured onto ice water containing 3.0 g of ammonium chloride. The resulting mixture was extracted with ethyl acetate. The extract was dried (MgSO$_4$) and concentrated to dryness. The residue, a pale yellow oil, was dissolved in chloroform and passed through a column of silica gel. The eluate was evaporated to give a colorless oil. Crystallization of the oil from hexane gave the title compound; mp 95°–97° C.; NMR (CDCl$_3$)δ 1.25 (d, J=6.3 Hz, 3H), 2.55 (s, 3H), 3.70 & 3.75 (2s, 6H), 4.4 (t, J=3.8 Hz, 1H), 6.35 (s, 1H), 7.2 (m, 4H); Anal Calcd for C$_{21}$H$_{25}$NO$_2$: C, 77.98% H, 7.79% N, 4.33%; Found: C, 78.03% H, 8.05% N, 4.12%.

By following the procedure of example 6 and by selecting the appropriate Grignard reagent of formula R$^2$MgX in which R$^2$ is lower alkyl, lower cycloalkyl, phenyl or phenylmethyl and X is halo, other key intermediates of formula III in which R$^1$ is methyl, R$^2$ is the organic radical which is equivalent to the organic radical of the Grignard reagent employed, R$^6$ and R$^7$ are both methoxy and R$^8$ is hydrogen are obtained. Examples of such compounds of formula III are listed in Table I together with the Grignard reagent used for their preparation.

TABLE I

| Example | Grignard reagent | Yield | Product:(prefix listed below)-1,2,3,7,8,12b-hexahydrobenzo[6,7]cyclohepta[1,2,3-de]isoquinoline |
|---|---|---|---|
| 7 | C$_2$H$_5$MgI | 74% | (3,12b-trans)-3-ethyl-4,5-dimethoxy-2-methyl; mp 103–104° C.; NMR (CDCl$_3$ δ 0.9 (t, J = 7 Hz, 3H), 2.56 (s, 3H), 3.70 (s, 3H), 3.75 (s,3H), 4.5 (t, J = 5 Hz, 1H), 6.4 (s, 1H), 7.1 (m, 4H) |
| 8 | n-C$_3$H$_7$MgI | 91% | (3,12b-trans)-4,5-dimethoxy-2-methyl-3-propyl; mp 119–120° C.; NMR (CDCl$_3$) δ 0.9 (t, J = 6.8 Hz, 3H), 1.55 (m, 4H), 2.57 (s,3H), 3.70 & 3.75 (2s, 6H), 4.5 (t, J = 5, 1H), 7.2 (m, 4H) |
| 9 | i-C$_3$H$_7$MgI | 55% | (3,12b-trans)-4,5-dimethoxy-2-methyl-3-(l-methylethyl); mp 99–101° C.; NMR (CDCl$_3$) δ 0.65 (d, J = 6.5 Hz, 3H), 1.0 (d, J = 6.5 Hz, 3H), 2.6 (s, 3H), 3.65 & 3.75 (2s, 6H), 4.42 (t, J = 5 Hz, 1H), 6.35 (s, 1H), 7.1 (m,4H) |
| 10 | C$_6$H$_5$CH$_2$MgCl | 65% | (3,12b-trans)-4,5-dimethoxy-2-methyl-3-(phenylmethyl); mp 141–142° C.; NMR (CDCl$_3$) δ 2.75 (s, 3H), 3.3 (s, 6H), 3.65 (s, 2H), 4.4 (m, 1H), 5.55 (s, 1H), 7.1 (m, 9H) |
| 11 | (CH$_2$)$_4$CHMgBr | 63% | (3,12b-trans)-3-cyclopentyl-4,5-dimethoxy-2-methyl; mp 134–135° C.; NMR (CDCl$_3$) δ 1.46 (m, 4H), 2.63 (s, 3H), 3.65 & 3.73 (2s, 6H), 4.40 (t, J = 4 Hz, 1H), 6.36 (s, H), 7.05 & 7.30 (2m, 4H) |
| 12 | C$_6$H$_5$MgBr | 73% | (3,12b-trans)-4,5-dimethoxy-2-methyl-3-phenyl; mp 154–156° C.; NMR (CDCl$_3$) δ 2.30 (s, 3H), 3.50 (s, 3H), 3.67 (s, 3H), 4.55 (s, 1H), 4.75 (t, J = 5.5 Hz, 1H), 6.05 (s, 1H), 7.2 (m, 9H) |

By selecting the appropriate starting material of formula II, preparing its corresponding quaternary salt according to the procedure of step (a) of examples 4 or 5 with the appropriate organohalide, and reacting the quaternary salt with the appropriate Grignard reagent according to the procedure of example 6, still other compounds of formula III are obtained. Examples of such compounds are listed in examples 12a to 12d:

EXAMPLE 12a

By following serially the procedure of step (a) of example 4 and the procedure of example 6, and selecting 4,5-dimethoxy-1,7,8,12b-tetrahydrobenzo[6,7]cyclohepta[1,2,3-de]isoquinoline (described in example 2) as the starting material of formula II, ethyl iodide as the organohalide and ethyl magnesium iodide as the Grignard reagent, (3,12b-trans)-2,3-diethyl-4,5-dimethoxy-1,2,3,7,8,12b-hexahydrobenzo[6,7]cyclohepta[1,2,3-de]isoquinoline, mp 109°–110° C., NMR (CDCl$_3$)δ 0.95 (t, J=7 Hz, 3H), 1.25 (1.25, J=7 Hz, 3H), 3.70 (s, 3H), 3.75 (s, 3H), 4.45 (t, J=3.8 Hz, 1H), 6.40 (s, 1H), 7.2 (m, 4H), was obtained via the 2-ethyl quaternary salt described in example 4a.

EXAMPLE 12b

By following serially the procedure of step (a) of example 5 and the procedure of example 6, and selecting 5,6-dimethoxy-1,7,8,12b-tetrahydrobenzo[6,7]cyclohepta[1,2,3-de]isoquinoline (described in example 2) as the starting material of formula II, methyl iodide as the organohalide and ethyl magnesium bromide as the Grignard reagent, (3,12b-trans)-3-ethyl-5,6-dimethoxy-2-methyl-1,2,3,7,8,12b-hexahydrobenzo[6,7]cyclohepta[1,2,3-de]isoquinoline, mp 92°–94° C., was obtained via 5,6-dimethoxy-2-methyl-1,7,8,12b-tetrahydrobenzo[6,7]cyclohepta[1,2,3-de]-isoquinolinium iodide, mp 195°–210° C., NMR (DMSO-d$_6$) δ 3.83 (s, 3H), 3.88 (s, 3H), 3.97 (s, 3H), 4.42 (m, 2H), 5.18 (m, 1H), 7.10 (m, 4H), 7.38 (s, 1H), 9.17 (s, 1H).

EXAMPLE 12c

By following serially the procedure of step (a) of example 5 and the procedure of example 6 and selecting 5,6-dimethoxy-1,7,8,12b-tetrahydrobenzo[6,7]cyclohepta[1,2,3-de]isoquinoline as the starting material of formula II, methyl iodide as the organohalide and phenylmethyl magnesium chloride as the Grignard reagent, (3,12b-trans)-5,6-dimethoxy-2-methyl-3-(phenylmethyl)-1,2,3,7,8,12b-hexahydrobenzo[6,7]cyclohepta[1,2,3-de]isoquinoline, mp 154°–156° C., NMR (CDCl$_3$) δ2.4 (s, 3H), 3.77 & 3.85 (2s, 6H), 6.5 (s, 1H), 7.2 (m, 9H), was obtained via 5,6-dimethoxy-2-methyl-1,7,8,12b-tetrahydrobenzo[6,7]cyclohepta[1,2,3-de]isoquinolinium iodide, mp 195°–210° C. (dec), NMR (DMSO-d$_6$) δ 3.83 (s, 3H), 3.88 (s, 3H), 3.97 (s, 3H), 4.42 (m, 2H), 5.18 (m, 1H), 7.10 (m, 4H), 7.38 (s, 1H), 9.17 (s, 1H).

EXAMPLE 12d

By following serially the procedure of step (a) of example 5 and the procedure of example 6 and selecting 5,6-dimethoxy-1,7,8,12b-tetrahydrobenzo[6,7]cyclohepta[1,2,3-de]isoquinoline as the starting material of formula II, benzyl bromide as the organohalide and methyl magnesium iodide as the Grignard reagent, (3,12b-trans)-5,6-dimethoxy-3-methyl-2-(phenylmethyl)-1,2,3,7,8,12b-hexahydrobenzo[6,7]cyclohepta[1,2,3-de]isoquinoline, mp 160°–162° C., NMR (CDCl$_3$) δ6.5 (s, 1H), 7.25 (m, 9H), was obtained via 5,6-dimethoxy-2-phenylmethyl-1,7,8,12b-tetrahydrobenzo-[6,7]cyclohepta[1,2,3-de]isoquinolinium bromide, mp 196° C. (dec), NMR (DMSO-d$_6$) δ 3.85 & 3.95 (2s, 6H), 5.15 (m, 1H), 5.32 & 5.62 (2d, J=13.7 Hz, 2H), 6.1–7.8 (m, 10H), 9.6 (s, 1H).

EXAMPLE 13

(3,12b-trans)-5,6-Dimethoxy-3-methyl-1,2,3,7,8,12b-hexahydrobenzo[6,7]cyclohepta[1,2,3-de]isoquinoline (III; R$^1$ and R$^8$=H, R$^2$=CH$_3$, and R$^3$ and R$^4$=OCH$_3$)

A mixture of (3,12b-trans)-5,6-dimethoxy-3-methyl-2-(phenylmethyl)-1,2,3,7,8,12b-hexahydrobenzo[6,7]cyclohepta[1,2,3-de]isoquinoline (0.580 g, 1.7 mmol, described in example 12d), acetic acid (5 mL) and 10% (w/w) palladium on charcoal (100 ml) was stirred in an atmosphere of hydrogen at 20°–22° C. (at normal pressure). Thereafter, the reaction mixture was filtered through cellulose powder. The filter cake was washed with ethyl acetate. The combined filtrate was cooled in an ice bath and made basic with concentrated ammonium hydroxide. The organic layer was separated, washed with water, dried (MgSO$_4$) and evaporated to dryness to give the title compound as a colorless foam (459 mg); NMR (CDCl$_3$) δ 1.45 (d, J=6.5 Hz, 3H), 1.8 (s, 1H), 3.75 & 3.77 (2s, 6H), 4.3 (m, 2H), 6.55 (s, 1H), 7.2 (m, 4H).

The corresponding hydrochloride of the title compound had mp 266°–268° C.; NMR (DMSO-d$_6$)δ 1.55 (d, J=6.5 Hz, 3H), 3.73 & 3.75 (2s, 6H), 4.6 (m, 1H), 4.9 (m, 1H), 6.8 (s, 1H), 7.15 (m, 4H), 9.6 (broad, 2H); Anal Calcd for C$_{20}$H$_{23}$NO$_2$.HCl: C, 69.45% H, 6.99% N, 4.05%; Found: C, 69.15% H, 7.17% N, 4.00%.

EXAMPLE 14

1,2,3,7,8,12b-Hexahydrobenzo[6,7]cyclohepta[1,2,3-de]isoquinoline-4,5-diol hydrobromide (the hydrogen bromide addition salt of I; R$^1$, R$^2$ and R$^5$=H and R$^3$ and R$^4$=OH)

A mixture of the di(lower alkoxy) compound, 4,5-dimethoxy-1,2,3,7,8,12b-hexahydrobenzo[6,7]cyclohepta[1,2,3-de]isoquinoline hydrochloride (250 mg, 0.76 mmol, described in example 3) and 47–49% (v/w) hydrobromide acid was heated at reflux for 2 days (oil bath temperature=160° C.). The reaction mixture was cooled to 20°–22° C. The solid in the mixture was collected on a filter. The collected solid washed with ethyl acetate and diethyl ether, and then recrystallized twice from a mixture of methanol and diethyl ether to give the pure title compound (140 mg); mp 314°–317° C.; NMR (DMSO-d$_6$) δ 2.50–4.00 (m, 6H), 4.12 (s, 2H), 4.90 (t, J=7 Hz, 1H), 6.40 (s, 1H), 7.19 (s, 4H), 8.18 (s, 1H), 9.05 (broad, 2H), 9.28 (s, 1H); Anal Calcd for C$_{17}$H$_{17}$NO$_2$.HBr: C, 58.63% H, 5.21% N, 4.02%; Found: C, 58.69% H, 5.34% N, 4.05%.

EXAMPLE 15

2-Methyl-1,2,3,7,8,12b-hexahydrobenzo[6,7]cyclohepta[1,2,3-de]isoquinoline-4,5-diol hydrobromide (the hydrogen bromide addition salt of I; R$^1$=CH$_3$, R$^2$ and R$^5$=H and R$^3$ and R$^4$=OH)

Under nitrogen, boron tribromide (1.7 mL, 4.5 g, 18 mmol) was added dropwise to a stirred solution of the di(lower)alkoxy compound, 4,5-dimethoxy-2-methyl-1,2,3,7,8,12b-hexahydrobenzo[6,7]cyclohepta[1,2,3-de]isoquinoline (1.15 g, 3.7 mmol, described in example 4) in chloroform (25 mL) at 10° C. The reaction mixture was stirred at 20°–22° C. for 3 hr. Stirring was continued while the reaction mixture was cooled to 0° C. and subjected to the dropwise addition of ethanol (25 mL). The reaction mixture was stirred at 0° C. for an additional hr. and then diluted with diethyl ether. The solid in the reaction mixture was collected, washed with diethyl ether and crystallized from boiling methanol-diethyl ether to give the title compound; mp 300°–302° C.; NMR (DMSO-d$_6$) δ 2.55 (s, 3H); 5.03 (t, J=6 Hz, 1H), 6.43 (s, 1H), 7.20 (s, 4H), 8.20 (s, 1H), 9.32 (s, 1H), 10.0 (s, 1H); Anal Calcd for C$_{18}$H$_{19}$NO.HBr: C, 59.68% H, 5.56% N, 3.87; Found: C, 59.55% H, 5.61% N, 3.88%.

By following the procedure of example 14 or 15 and using the appropriate di(lower) alkoxy compound of formula I in which R$^1$ and R$^2$ are as defined herein, and either R$^3$ and R$^4$ are both methoxy and R$^5$ is hydrogen, or R$^3$ is hydrogen and R$^4$ and R$^5$ are both methoxy, as the starting material; other dihydroxy compounds of formula I are obtained. Examples of such dihydroxy compounds are listed in Tables II and III.

TABLE II

| Example | Example in which starting material is prepared | Reagent and yield | Product: (prefix listed below)-1,2,3,7,8,12b-hexahydrobenzo[6,7]cyclohepta[1,2,3-de]isoquinoline-4,5-diol hydrobromide |
|---|---|---|---|
| 16 | 4a | 48% HBr, 55%; BBr$_3$, 89% | 2-ethyl; mp 280–281° C.; NMR (DMSO-d$_6$) δ 1.4 (t, J = 7 Hz, 3), 6.53 (s, 1H), 7.25 (s, 4H) |
| 17 | 4b | BBr$_3$, 73% | 2-propyl; mp 290–291° C.; NMR (DMSO-d$_6$) δ 0.96 (t, J = 7 Hz, 3H), 1.83 (m, 2H), 5.05 (t, 1H), 6.45 (s, 1H), 7.20 (s, 4H), 8.20 (s, 1H), 9.32 (s, 2H) |

TABLE II-continued

| Example | Example in which starting material is prepared | Reagent and yield | Product: (prefix listed below)-1,2,3,7,8,12b-hexahydrobenzo[6,7]cyclohepta[1,2,3-de]isoquinoline-4,5-diol hydrobromide |
|---|---|---|---|
| 18 | 4c | $BBr_3$, 73% | 2-(1-methylethyl); mp 181° C. (dec); NMR (CDCl$_3$) δ 1.4 (d, J = 6 Hz, 6H), 5.05 (m, 1H), 7.2 (m, 4H), 8.5 (s, 1H), 9.3 (s, 1H), 9.8 (m, 1H) |
| 19 | 4d | $BBr_3$, 70% | 2-(2-propenyl); mp 261–265° C.; NMR (DMSO-d$_6$) δ 3.5 (m, 8H), 4.25 (s, 2H), 5.0 (m, 1H), 5.8 (m, 3H), 6.45 (s, 1H), 7.15 (s, 4H), 8.13 (broad, 1H), the corresponding free base had NMR (CDCl$_3$) δ 3.25 (m, 10H), 4.6 (t, J = 5 Hz, 1H), 5.35 (m, 3H), 6.1 (s, 1H), 7.15 (m, 4H) |
| 20 | 4e | $BBr_3$, 58% | 2-(2-hydroxyethyl), also designated as 4,5-dihydroxy-1,2,3,7,8,12b-hexahydrobenzo[6,7]cyclohepta-[1,2,3-de]isoquinoline-2-ethanol hydrobromide); mp 280–282° C.; NMR (DMSO-d$_6$) δ 5.0 (m, 1H), 6.4 (s, 1H), 7.15 (m, 4H), 8.15 (s, 1H), 9.3 (s, 2H), 10.0 (broad, 1H) |
| 21 | 4f | $BBr_3$, 70% | 2-(phenylmethyl); mp 253–254° C.; NMR (DMSO-d$_6$) δ 2.5–4.4 (m, 10H), 4.55 (s, 2H), 4.95 (m, 1H), 6.4 (s, 1H), 7.2 (m, 3H), 7.5 (m, 6H), 9.3 (broad, 1H) |
| 22 | 6 | $BBr_3$, 63% | (3,12b-trans)-2,3-dimethyl; mp 300–301° C. (dec); NMR (DMSO-d$_6$) δ 1.5 (m, 3H), 2.9 (s, 3H), 4.5 (m, 1H), 5.0 (m, 1H), 6.45 & 7.15 (2m, 5H), 8.25 (s, 1H), 9.25 (s, 1H), 10.0 (b, 1H) |
| 23 | 7 | $BBr_3$, 56% | (3,12b-trans)-3-ethyl-2-methyl; mp 277–278° C.; NMR (DMSO-d$_6$) δ 0.80 & 1.05 (2t, J = 7, 3H), 3.00 (s, 3H), 5.05 (broad, 1H), 6.45 & 6.56 (2s, 1H), 7.20 (m, 4H), 8.30 (s, 1H), 9.30 (s, 2H); the corresponding hydrochloride had mp 270–273° C. |
| 24 | 8 | $BBr_3$, 58% | (3,12b-trans)-2-methyl-3-propyl; mp 268–271° C. (dec); NMR (DMSO-d$_6$) δ 0.95 (m, 3H), 1.7 (m, 4H), 3.0 (s, 3H), 5.0 (m, 1H), 6.5 & 7.2 (2m, 5H), 8.25 (s, 1H), 9.25 (s, 1H) |
| 25 | 9 | $BBr_3$, 90% | (3,12b-trans)-2-methyl-3-(1-methylethyl); mp (sintering at 150° C.); NMR (DMSO-d$_6$) δ 0.60 (d, j = 6.5 Hz, 3H), 1.1 (m, 4H), 4.9 (m, 1H), 6.45 (d, 1H), 7.2 (s, 4H), 8.3 (broad, 1H), 9.3 (broad, 2H) |
| 26 | 10 | $BBr_3$, 80% | (3,12b-trans)-2-metyl-3-(phenylmethyl); mp 255–257° C. (dec); NMR (DMSO-d$_6$) δ 3.05 (s, 3H), 5.95 (s, 1H), 7.25 (m, 9H), 8.25 (broad, 1H), 9.10 (broad, 1H), 11.2 (broad, 1H) |
| 27 | 11 | $BBr_3$, 65% | (3,12b-trans)-3-cyclopentyl-2-methyl; mp 255–257° C.; NMR (DMSO-d$_6$) δ 1.55 (m, 11H), 3.05 (d, J = 3 Hz, 3H), 6.5 (s, 1H), 7.2 (m, 4H), 8.3 (broad, 1H), 9.3 (s, 1H), 9.8 (broad, 1H) |
| 28 | 12 | $BBr_3$, 84% | (3,12b-trans)-2-methyl-3-phenyl; mp 285–287° C. (dec) NMR (DMSO-d$_6$) δ 2.75 (s, 3H), 5.40 (m, 1H), 5.75 (s, 1H), 7.35 (m, 9H), 9.2 (broad, 1H), 10.4 (broad, 1H) |
| 29 | 12a | $BBr_3$, 88% | (3,12b-trans)-2,3-diethyl; mp 265–267° C. (dec); NMR (DMSO-d$_6$) δ 1.00 (t, J = 7 Hz, 3H), 1.40 (t, J = 7 Hz, 3H), 6.45 (s, 1H), 7.2 (m, 4H), 8.25 (s, 1H), 9.30 (s, 1H), 9.50 (broad, 1H) |

TABLE III

| Example | Example in which starting material is prepared | Reagent and yield | Product: (prefix listed below)-1,2,3,7,8,12b-hexahydrobenzo[6,7]-cyclohepta[1,2,3-de]isoquinoline-5,6-diol hydrobromide |
|---|---|---|---|
| 30 | 3a | BBr$_3$, 70% | *; mp 314–315° C.; NMR (DMSO-d$_6$) δ 2.5–4.1 (m, 8H), 4.75 (t, J = 6 Hz, 1H), 6.5 (s, 1H), 7.2 (s, 4H), 8.55 (s, 1H), 9.0 (broad, 2H), 9.2 (s, 1H) |
| 31 | 5a | BBr$_3$, 85% | 2-ethyl; mp 281° C. (dec); NMR (DMSO-d$_6$) δ 1.4 (t, J = 7 Hz, 3H), 5.0 (m, 1H), 6.5 & 7.15 (m, 5H), 8.65 (s, 1H), 9.25 (s, 1H), 9.8 (m, 1H) |
| 32 | 12b | BBr$_3$, 86% | (3,12b-trans)-3-ethyl-2-methyl; mp 267–270° C. (dec); NMR (DMSO-d$_6$) δ 1.0 (t, J = 7 Hz, 3H), 3.1 (s, 3H), 4.4 (broad, 1H), 4.93 (broad, 1H), 6.55 (s, 1H), 7.15 (s, 4H), 8.65 (s, 1H), 9.3 (s, 1H), 9.6 (broad, 1H) |
| 33 | 12c | BBr$_3$, 78% | (3,12b-trans)-2-methyl-3-(phenylmethyl); mp 170° C. (dec); NMR (DMSO-d$_6$) δ 2.80 (s, 3H), 6.65 (s, 1H), 7.2 (m, 9H), 8.95 (s, 1H), 9.40 (s, 1H), 9.70 (broad, 1H) |
| 34 | 13 | BBr$_3$, 97% | (3,12b-trans)-3-methyl; mp 302–303° C. (dec); NMR DMSO-d$_6$) δ 1.55 (d, J = 6.5 Hz, 3H), 2.5–4.0 (m, 6H), 4.55 (m, 1H), 4.8 (m, 1H), 6.6 (s, 1H), 7.5 (m, 4H), 10.75 (s, 1H), 11.25 (broad, 2H), 11.5 (s, 1H) |

*No prefix as compound is 1,2,3,7,8,12b-hexahydrobenzo[6,7]cycolohepta[1,2,3-de]-isoquinoline-5,6-diol hydrobromide

EXAMPLE 35

5-Methoxy-1,2,3,7,8,12b-hexahydrobenzo[6,7]cyclohepta[1,2,3-de]isoquinolin-4-ol hydrochloride (the hydrogen chloride addition salt of I; R$^1$, R$^2$ and R$^5$=H, R$^3$=OH and R$^4$=OCH$_3$)

A suspension of the di(lower)alkoxy compound, 4,5-dimethoxy-1,2,3,7,8,12b-hexahydrobenzo[6,7]cyclohepta[1,2,3-de]isoquinoline (0.98 g, 3.3 mmol, described in example 3), in concentrated hydrochloric acid (10 mL) was stirred and heated at reflux for 58 hr. (oil bath temperature=130° C.). The reaction mixture was cooled and the solid therein was collected. The solid (0.65 g) was partitioned between concentrated ammonium hydroxide and ethyl acetate. The organic layer was separated, dried (MgSO$_4$) and evaporated to dryness. The residue was dissolved in chloroform-methanol (19:1, v/v) and passed through a column of silica gel. The eluate was evaporated. The residue (400 mg) was dissolved in a minimum amount of chloroform. A saturated solution of hydrogen chloride in diethyl ether was added to the chloroform solution. Collection of the resulting solid gave the title compound, mp 300°–303° C.

The corresponding free base had NMR (CDCl$_3$) δ3.2 (m, 4H), 3.8 (s, 3H), 4.0 (m, 4H), 4.5 (t, 1H), 6.4 (s, 1H), 7.3 (m, 4H).

EXAMPLE 36

5-Methoxy-2-methyl-1,2,3,7,8,12b-hexahydrobenzo[6,7-]cyclohepta[1,2,3-de]isoquinolin-4-ol (I; R$^1$=CH$_3$, R$^2$ and R$^5$=H, R$^3$=OH and R$^4$=OCH$_3$)

A suspension of the di(lower)alkoxy compound, 4,5-dimethoxy-2-methyl-1,2,3,7,8,12b-hexahydrobenzo[6,7-]cyclohepta[1,2,3-de]isoquinoline (1.0 g, 3.2 mmol, described in example 4) in 58% (v/w) hydriodic acid (30 mL) was stirred in a closed vessel for 3 weeks at 20°–22° C. The reaction mixture was poured into ice water (50 mL). The resulting precipitate was collected, washed with a small amount of water, and then partitioned between concentrated ammonium hydroxide-water (1:1, v/v) and ethyl acetate. The organic phase was separated, washed with brine, dried (MgSO$_4$) and evaporated to dryness to give the title compound as a yellow solid. The product was purified by converting it to its hydrochloride and then regenerating the free base (0.864 g) from the hydrochloride. When purified in this manner and recrystallized from chloroform-hexane, the title compound had mp 173°–174° C.; NMR (CDCl$_3$) δ2.50 (s, 3H), 3.75 (s, 3H), 4.55 (m, 1H), 5.50 (broad, 1H), 6.34 (s, 1H), 7.10 (m, 3H), 7.50 (m, 1H); Anal Calcd for C$_{19}$H$_{21}$NO$_2$: C, 77.26% H, 7.17% N, 4.74%; Found: C, 77.36% H, 7.23% N, 4.68%.

The corresponding hydrochloride had mp 173°–174° C.

EXAMPLE 37

(3,12b-trans)-5-Methoxy-2-methyl-3-(phenylmethyl)-1,2,3,7,8,12b-hexahydrobenzo[6,7]-cyclohepta[1,2,3-de]isoquinolin-4-ol (I; R$^1$=CH$_3$, R$^2$=CH$_2$C$_6$H$_5$, R$^3$=OH, R$^4$=OCH$_3$ and R$^5$=H)

A mixture of (3,12b-trans)-4,5-dimethoxy-2-methyl-3-(phenylmethyl)-1,2,3,7,8,12b-hexahydrobenzo[6,7]cyclohepta[1,2,3-de]isoquinoline (1.4 g, 3.5 mmol, described in example 10), methionine (0.580 g, 3.9 mmol) and methanesulfonic acid (4.6 mL, 70 mmol) was stirred at 20°–22° C. for 48 hr. The reaction mixture was poured onto ice. The resulting mixture was made basic with concentrated ammonium hydroxide and extracted with ethyl acetate. The extract was dried (MgSO$_4$) and evaporated to dryness. The residue (1.4 g) was dissolved in benzene and the solution was poured onto a column of silica gel. Elution of the column with benzene-acetone (19:1, v/v) and concentration of the eluates gave the title compound (1.1 g) as a white solid. Recrystallization from chloroform and then diethyl ether-hexane gave the pure title compound; mp 168°–171° C.; NMR (CDCl$_3$) δ 2.75 (s, 3H), 3.30 (s, 3H), 3.90 (m, 1H), 4.45 (s, 1H), 5.45 (s, 2H), 7.1 (m, 9H); Anal Calcd for C$_{26}$H$_{27}$NO$_2$: C, 81.01% H, 7.06% N, 3.63%; Found: C, 80.94% H, 7.35% N, 3.55%.

The corresponding hydrochloride of the title compound had mp 170° C. (dec); NMR (DMSO-d$_6$) δ 3.00 (s, 3H), 3.30 (s, 3H), 4.70 (m, 1H), 5.1 (s, 1H), 5.8 (s, 1H), 7.3 (m, 9H), 8.5 (broad, 2H).

By following the procedure of example 35, 36 or 37 and using the appropriate di(lower)alkoxy compound of formula I in which R$^1$ and R$^2$ are as defined herein, and either R$^3$ and R$^4$ are both methoxy and R$^5$ is hydrogen, or R$^3$ is hydrogen and R$^4$ and R$^5$ are both methoxy, as the starting material; other selectively dealkylated compounds of formula I in which R$^1$ and R$^2$ are as defined herein, R$^4$ is methoxy, and either R$^3$ is hydroxy and R$^5$ is hydrogen or R$^3$ is hydrogen and R$^5$ is hydroxy, are obtained. Examples of such selectively dealkylated compounds are listed in Tables IV and V.

TABLE IV

| Example | Example in which starting material is prepared | Procedure* and yield | Product: (prefix listed below) 1,2,3,7,8,12b-hexahydrobenzo[6,7]-cyclohepta[1,2,3-de]isoquinolin-4-ol |
|---|---|---|---|
| 38 | 4a | A, 78% | 2-ethyl-5-methoxy; mp 146–148° C.; NMR (CDCl$_3$) δ 1.3 (t, J = 7 Hz, 3H), 2.45–3.95 (m, 10H), 3.7 (s, 3H), 4.6 (t, J = 3.5 Hz, 1H), 5.42 (s, 1H), 6.45 (s, 1H), 7.15 (m, 3H) 7.65 (m, 1H); the corresponding hydrochloride had mp 246° C. (dec) |
| 39 | 4b | B, 75% | 5-methoxy-2-propyl; 142–143° C.; NMR (CDCl$_3$) δ 1.00 (t, J = 7 Hz, 3H), 1.72 (m, 2H), 3.71 (s, 3H), 4.50 (t, 1H), 5.45 (broad, 1H), 6.28 (s, 1H), 7.05 (m, 3H), 7.55 (m, 1H); the corresponding hydrochloride had mp 239–241° C. (dec) |
| 40 | 4c | B, 35% | 5-methoxy-2-(1-methylethyl); mp 153–156° C.; NMR (CDCl$_3$) δ 1.22 (d, J = 6 Hz, 6H), 2.95 (m, 4H), 3.75 (s, 3H), 4.65 (m, 1H), 5.48 (s, 1H), 6.35 (s, 1H), 7.10 (m, 3H), 7.60 (m, 1H); the corresponding hydrochloride had mp 220–224° C. |
| 41 | 4d | B, 79% | 5-methoxy-2-(2-propenyl); NMR (CDCl$_3$) δ 1.5 (broad, 1H), 3.75 (s, 3H), 4.55 (m, 1H), 5.6 (m, 3H), 6.35 (s, 1H), 7.25 (m, 4H); the corresponding hydrochloride had mp 228–234° C. (dec) |
| 42 | 4e | B, 50% | 2-(2-hydroxyethyl)-5-methoxy (also designated as 4-hydroxy-5-methoxy-1,2,3,7,8,12b-hexahydro-benzo[6,7]cyclohepta[1,2,3-de]iso-quinoline-2-ethanol); mp 145–147° C.; NMR (CDCl$_3$) δ 3.75 (s, 3H), 4.55 (m, 1H), 5.3 (s, 1H), 7.05 (m, 3H), 7.4 (m, 1H) |
| 43 | 4f | B, 60% | 5-methoxy-2-(phenylmethyl); mp 148–150° C.; NMR (CDCl$_3$) δ 3.7 (s, 3H), 4.55 (m, 1H), 5.47 (s, 1H), 6.25 (s, 1H), 7.3 (m, 9H) |
| 44 | 7 | B, 68% | (3,12b-trans)-3-ethyl-5-methoxy-2-methyl; mp 172–174° C.; NMR (CDCl$_3$) δ 0.88 (t, J = 7 Hz, 3H), 2.55 (s, 3H), 3.75 (s, 3H), 4.55 (t, J = 5 Hz, 1H), 5.45 (s, 1H), 6.4 (s, 1H), 7.1 (m, 3H), 7.3 (m, 1H); the corresponding hydrochloride had mp 204–206° C. (dec) |

*A indicates that the procedure of example 35 was employed
B indicates that the porocedure of example 36 was employed

TABLE V

| Example | Example in which starting material is prepared | Procedure* and yield | Product: (prefix listed below)-1,2,3,7,8,12b-hexahydrobenzo[6,7]-cyclohepta[1,2,3-de]isoquinolin-6-ol |
|---|---|---|---|
| 45 | 3a | B, 20% | 5-methoxy; mp 210–212° C.; NMR (CDCl$_3$) δ 3.8 (s, 3H), 6.5 (s, 1H), 7.1 (m, 3H), 7.45 (m, 1H) |

TABLE V-continued

| Example | Example in which starting material is prepared | Procedure* and yield | Product: (prefix listed below)-1,2,3,7,8,12b-hexahydrobenzo[6,7]-cyclohepta[1,2,3-de]isoquinolin-6-ol |
|---|---|---|---|
| 46 | 5 | C, 50% | 5-methoxy-2-methyl; mp 197–200° C. (dec); NMR (CDCl₃) δ 2.55 (s, 3H), 3.75 (s, 3H), 4.5 (m, 1H), 5.45 (s, 1H), 6.55 (s, 1H), 7.0 (m, 2H), 7.4 (m, 2H) |
| 47 | 5a | B, 30% | 2-ethyl-5-methoxy; mp 169–172° C. (dec); NMR CDCl₃) δ 1.28 (t, J = 7 Hz, 3H), 3.75 (s, 3H), 4.5 (t, J = 3.8 Hz, 1H), 5.4 (s, 1H), 6.4 (s, 1H), 7.05 (m, 3H), 7.55 (m, 1H) |
| 48 | 12b | C, 68% | (3,12b-trans)-3-ethyl-5-methoxy-2-methyl; mp 114–115° C.; NMR (CDCl₃) δ 1.05 (t, J = 7 Hz, 3H), 2.65 (s, 3H), 3.75 (s, 3H), 4.0 (t, J = 4.25 Hz, 1H), 4.4 (t, J = 3.75 Hz, 1H), 5.45 (s, 1H), 6.4 (s, 1H), 7.2 (m, 4H) |
| 49 | 12c | C, 60% | (3,12b-trans)-5-methoxy-2-methyl-3-(phenylmethyl); mp 183–186° C.; NMR (CDCl₃) δ 2.40 (s, 3H), 3.15 (m, 8H), 3.75 (s, 3H), 4.35 (m, 1H), 4.60 (m, 1H), 6.45 (s, 1H), 7.2 (m, 9H); the corresponding hydrochloride had mp 165° C. |

*B indicates that the procedure of example 36 was employed
C indicates that the procedure of example 37 was employed

We claim:
1. A compound of formula I

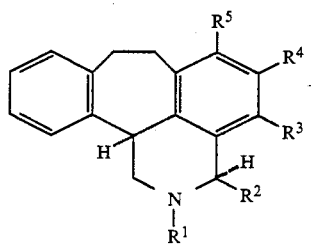

(I)

in which $R^1$ is hydrogen, lower alkyl, lower alkenyl, hydroxy(lower)alkyl or phenylmethyl; $R^2$ is hydrogen, lower alkyl, lower cycloalkyl, phenyl or phenylmethyl; $R^4$ is lower alkoxy or hydroxy; and $R^3$ is hydroxy and $R^5$ is hydrogen, or $R^3$ is hydrogen and $R^5$ is hydroxy; wherein lower alkyl and lower alkenyl are straight chain alkyl radicals having from 1 to 6 carbon atoms and branched chain alkyl radicals having up to 4 carbon atoms and lower cycloalkyl are cyclic alkyl radicals having 3 to 6 carbon atoms or a therapeutically acceptable acid addition salt thereof.

2. The compound of claim 1 in which $R^1$ is lower alkyl having one or two carbon atoms; $R^2$ is hydrogen, lower alkyl having one to three carbon atoms, phenyl or phenylmethyl; or a therapeutical acceptable acid addition salt thereof.

3. The compound of claim 2 in which $R^1$ is methyl; $R^2$ is methyl, ethyl, 1-methylethyl or phenylmethyl; $R^4$ is methoxy or hydroxy; $R^3$ is hydroxy and $R^5$ is hydrogen, or $R^3$ is hydrogen and $R^5$ is hydroxy; or a therapeutically acceptable acid addition salt thereof.

4. The compound of claim 3 in which $R^2$ is ethyl or phenylmethyl, $R^3$ is hydroxy, $R^4$ is methoxy and $R^5$ is hydrogen, or a therapeutically acceptable salt thereof.

5. 2-(Phenylmethyl)-1,2,3,7,8,12b-hexahydrobenzo[6,7]cyclohepta[1,2,3-de]isoquinoline-4,5-diol, as claimed in claim 1.

6. (3,12b-trans)-2,3-Dimethyl-1,2,3,7,8,12b-hexahydrobenzo[6,7]cyclohepta[1,2,3-de]isoquinoline-4,5-diol, as claimed in claim 3.

7. (3,12b-trans)-3-Ethyl-2-methyl-1,2,3,7,8,12b-hexahydrobenzo[6,7]cyclohepta[1,2,3-de]isoquinoline-4,5-diol as claimed in claim 3.

8. (3,12b-trans)-2-Methyl-3-propyl-1,2,3,7,8,12b-hexahydrobenzo[6,7]cyclohepta[1,2,3,-de]isoquinoline-4,5-diol, as claimed in claim 2.

9. (3,12b-trans)-2-Methyl-3-(1-methylethyl)-1,2,3,7,8,12b-hexahydrobenzo[6,7]cyclohepta[1,2,3-de]isoquinoline-4,5-diol, as claimed in claim 3.

10. (3,12b-trans)-2-Methyl-3-(phenylmethyl)-1,2,3,7,8,12b-hexahydrobenzo[6,7]cyclohepta[1,2,3-de]isoquinoline-4,5-diol, as claimed in claim 3.

11. (3,12b-trans)-3-Ethyl-2-methyl-1,2,3,7,8,12b-hexahydrobenzo[6,7]cyclohepta[1,2,3-de]isoquinoline-5,6-diol, as claimed in claim 3.

12. (3,12b-trans)-2-Methyl-3-(phenylmethyl)-1,2,3,7,8,12b-hexahydrobenzo[6,7]cyclohepta[1,2,3-de]isoquinoline-5,6-diol, as claimed in claim 3.

13. (3,12b-trans)-5-Methoxy-2-methyl-3-(phenylmethyl)-1,2,3,7,8,12b-hexahydrobenzo[6,7]cyclohepta[1,2,3-de]isoquinolin-4-ol, as claimed in claim 4.

14. (3,12b-trans)-3-Ethyl-5-methoxy-2-methyl-1,2,3,7,8,12b-hexahydrobenzo[6,7]cyclohepta[1,2,3-de]isoquinolin-4-ol, as claimed in claim 4.

15. (3,12b-trans)-3-Ethyl-5-methoxy-2-methyl-1,2,3,7,8,12b-hexahydrobenzo[6,7]cyclohepta[1,2,3-de]isoquinolin-6-ol, as claimed in claim 3.

16. (3,12b-trans)-5-Methoxy-2-methyl-3-(phenylmethyl)-1,2,3,7,8,12b-hexahydrobenzo[6,7]cyclohepta[1,2,3-de]isoquinolin-6-ol, as claimed in claim 3.

17. A pharmaceutical composition useful for neuroleptic purposes comprising a compound of formula I

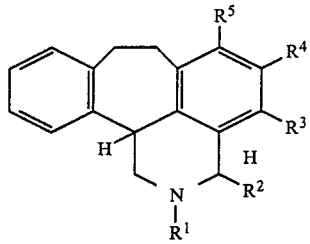
(I)

in which $R^1$ is hydrogen, lower alkyl, lower alkenyl, hydroxy(lower)alkyl or phenylmethyl; $R^2$ is hydrogen, lower alkyl, lower cycloalkyl, phenyl or phenylmethyl; $R^4$ is lower alkoxy or hydroxy; and $R^3$ is hydroxy and $R^5$ is hydrogen, or $R^3$ is hydrogen and $R^5$ is hydroxy; wherein lower alkyl and lower alkenyl are straight chain alkyl radicals having from 1 to 6 carbon atoms and branched chain alkyl radicals having up to 4 carbon atoms and lower cycloalkyl are cyclic alkyl radicals having 3 to 6 carbon atoms or a therapeutically acceptable acid addition salt thereof; and a pharmaceutically acceptable carrier wherein the compound of formula I is present at a neuroleptically effective amount.

18. The pharmaceutical composition of claim 17 in which the compound of formula I is one in which $R^1$ is methyl; $R^2$ is methyl, ethyl, 1-methylethyl or phenylmethyl; $R^4$ is methoxy or hydroxy; and $R^3$ is hydroxy and $R^5$ is hydrogen, or $R^3$ is hydrogen and $R^5$ is hydroxy.

19. The pharmaceutical composition of claim 17 in which the compound of formula I is one in which $R^1$ is methyl, $R^2$ is ethyl or phenylmethyl, $R^3$ is hydroxy, $R^4$ is methoxy and $R^5$ is hydrogen.

20. A method of producing neuroleptic effect in a mammal, without eliciting extrapyramidal syndrome, which comprises administering to said mammal an effective neuroleptic amount of the composition of claim 17.

* * * * *